United States Patent [19]

Shields

[11] Patent Number: 5,558,648

[45] Date of Patent: Sep. 24, 1996

[54] DISPOSABLE CONICAL HOLD FOR A MEDICINAL CARTRIDGE WITH REUSABLE PLUNGER AND SHIELDS

[76] Inventor: Jack W. Shields, 1950 Las Tunas Rd., Santa Barbara, Calif. 93103

[21] Appl. No.: 370,465

[22] Filed: Jan. 9, 1995

Related U.S. Application Data

[63] Continuation of Ser. No. 224,902, Apr. 8, 1994, abandoned.

[51] Int. Cl.⁶ .................................................. A61M 5/32
[52] U.S. Cl. ........................ 604/192; 604/198; 604/232
[58] Field of Search ................................ 604/187, 110, 604/192, 197, 198, 218, 263, 168, 195, 199, 194, 232, 233, 235, 241, 243, 239, 234; 128/919

[56] References Cited

U.S. PATENT DOCUMENTS

| | | | |
|---|---|---|---|
| 2,453,590 | 11/1948 | Poux | 604/263 X |
| 4,518,385 | 5/1985 | Lindmayer et al. | 604/48 |
| 4,583,978 | 4/1986 | Porat et al. | 604/208 |
| 4,767,413 | 8/1988 | Haber et al. | 604/198 |
| 4,969,877 | 11/1990 | Kornberg | 604/195 |
| 4,990,141 | 2/1991 | Byrne et al. | 604/198 |
| 5,024,616 | 6/1991 | Ogle, III | 604/192 |
| 5,135,514 | 8/1992 | Kimber | 604/240 |
| 5,176,657 | 1/1993 | Shields | 604/232 |
| 5,304,138 | 4/1994 | Mercado | 604/110 |
| 5,306,277 | 4/1994 | Bryant et al. | 606/93 |

FOREIGN PATENT DOCUMENTS

| | | | |
|---|---|---|---|
| 1718964 | 3/1992 | U.S.S.R. | 604/187 |
| 9218187 | 10/1992 | WIPO | 604/187 |

*Primary Examiner*—Randall L. Green
*Assistant Examiner*—V. Alexander

[57] ABSTRACT

A disposable hollow cylindroid in the form of a cone which wedge impacts an inserted piston-activated medicinal cartridge such that, employing one or two hands, the user can safely aspirate tissue fluid from a patient and inject contained fluid medications via a hollow needle. The leading end of this disposable hollow cylindroid comprises means for stabilizing the hollow needle serving the inserted cartridge. The trailing end is fitted with a separate reusable plunger whose leading end reversibly attaches to the trailing end of the cartridge piston. In operation, the user inserts the cartridge, uses a leading cylindrical cap on the plunger to wedge-impact the cartridge into the cone, attaches the plunger, screws the leading end of the plunger onto the trailing end of the cartridge piston, removes a sheathing cover from the hollow needle, aspirates into or injects fluid from the inserted cartridge, unscrews and extracts the plunger and, finally, discards the hollow cylindroid containing the cartridge and hollow needle into a safe container. An auxiliary shielding system is described to sterile-protect the cartridge before insertion and exposed sharp parts of the hollow needle after use in a patient.

8 Claims, 3 Drawing Sheets

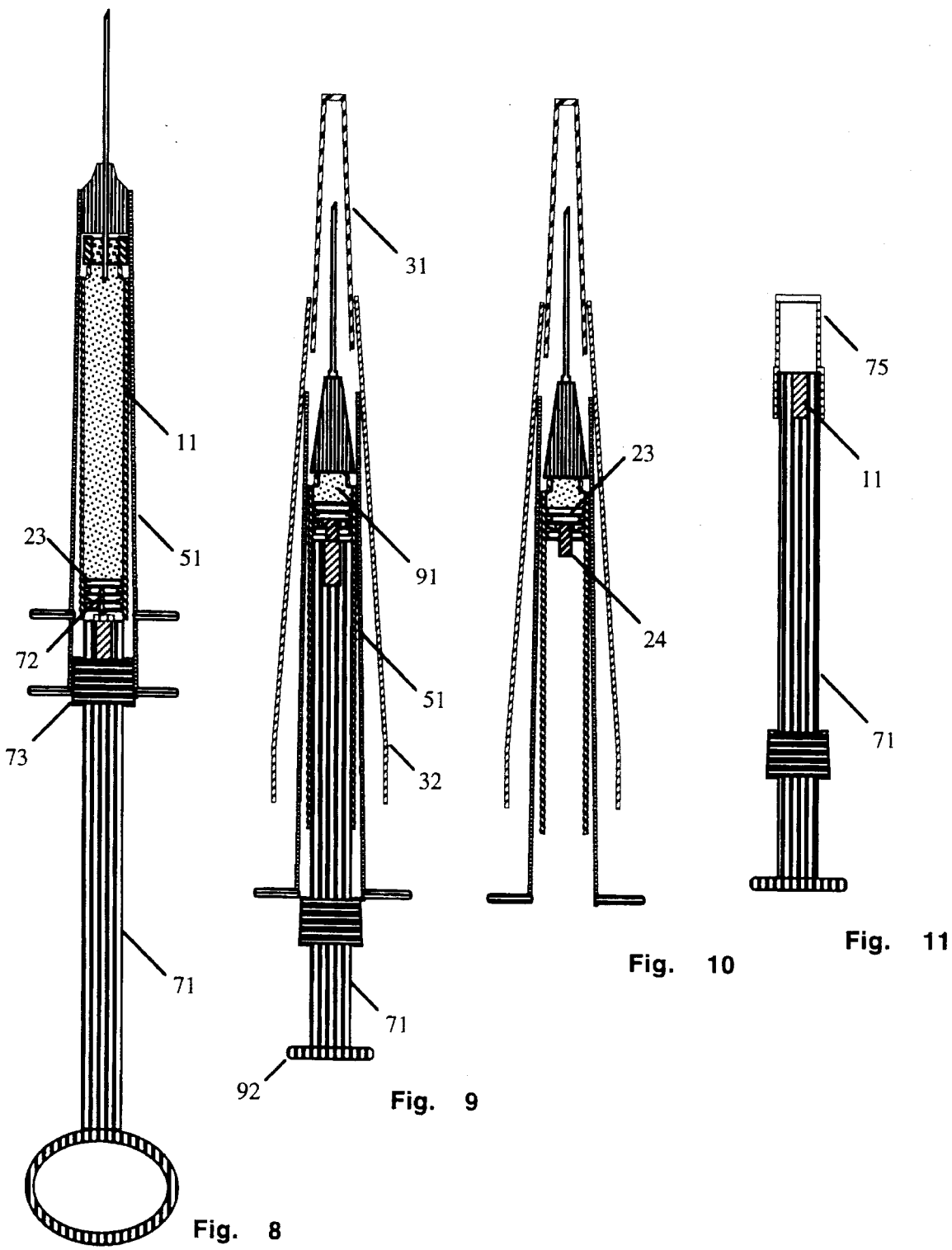

DISPOSABLE CONICAL HOLD FOR A MEDICINAL CARTRIDGE WITH REUSABLE PLUNGER AND SHIELDS

This is a continuation of U.S. Ser. No. 08/224,902, filed Apr. 8, 1994, now abandoned.

BACKGROUND OF INVENTION

1. Field of Invention

This invention relates to the convenient use of a fluid medication-filled cartridge inserted into a disposable cylindroid holder, such that the contents of the cartridge cannot become contaminated, while the user is protected from hollow-bore needle sticks. Such a device is sorely needed to protect users from hazardous needle sticks, and to protect patients from infectious disease hazards associated with the medical reuse of multiple dose vials, dental reuse of double-ended needles to empty more than one cartridge, and use of cylindrical containers whose leading caps are not sterile or tamper-proof. The device is especially designed toward preventing the transmission of HIV and HBV from patient to health care worker, from health care worker to patient and from patient to patient in health care settings.

2. Description of Prior Art

The use of disposable cylindric cartridges with reusable cylindric syringes having built-in plungers is customary in medical and dental practice. Being conical, lacking a built-in plunger and being disposable, the hollow cylindroid described here differs structurally from the prior syringe/cartridge art. The embodiment of one external trailing flange on the cylindroid is common in medical syringes, or two trailing flanges spaced a finger's breadth apart is common in dental syringes and in medical aspirating syringes designed for operation with one hand.

Means of hollow-bore steel needle attachment to the leading end of the hollow cylindroid or to the inserted pre-filled cartridge are well-known in the prior art. The dispensation of sterile cartridge in a three part puncture-resistant shielding system, the leading two parts of which are reused to protect the leading needle between uses, and before safe disposal was disclosed by Shields in U.S. Pat. No. 5,176,657 (01-05-93). The means of attaching a separate plunger to a fluid-filled cartridge is remindful of that in the Wyeth™ Tubex® system. However, the Tubex® system leaves the leading narrow end of the attached cartridge unprotected, is fragile and cannot be used inside the mouth. In the instant invention, wedge impaction of the leading shoulder of a cylindric gass cartridge in the leading conical bore of the hollow cylindroid not only avoids this problem, but also stabilizes the leading hollow-bore steel needle, prevents rotation of the cartridge when a separate plunger is reversibly attached to the trailing end of the cartridge piston and prevents the cartridge from falling out of the hollow cylindroid after use and safe disposal.

The separate reusable plunger is a versatile innovation, partly because it can be reused many times and partly because component parts are interchangeable, e.g. leading threaded receptacle, cork screw or harpoon; trailing thumb-ring or thumb-piece; and removable cap whose diameter can be varied. The sliding sleeve, however, must tightly fit the trailing bore of the hollow cylindroid in order to direct the thrust of the plunger and maintain stability of the entire; system, especially when used with a single hand.

The application of a needle which automatically recaps itself, cf. Kuracina et al in U.S. Pat. No. 4,998,933 issued 03/12/91, after use on the leading end of a cartridge or a syringe provides an alternative preferred embodiment, especially for medical, as opposed to dental usage.

SUMMARY

The object of this invention is to provide health care workers and their patients with an inexpensive, efficient, tamper-proof and safer system for giving sterile injections by means of a single-use cartridge and single-use needle which can be shielded safely before and after use, and disposed of conveniently, along with the hollow cylindroid which holds the cartridge and stabilizes the injection needle.

BRIEF DESCRIPTION OF THE DRAWINGS

FIG. 8 shows said plunger inserted into said hollow cylindroid and reversibly attached to said piston in said cartridge by means of said corkscrew.

FIG. 9 shows a spent cartridge inside said hollow cylindroid, after said hollow cylindroid is inserted into the remains of said three-part shielding system.

FIG. 10 shows a safely shielded disposable combination of the spent cartridge, leading hollow-bore steel needle, hollow cylindroid and shielding system after said plunger has been removed.

FIG. 11 shows said separate reusable plunger after a leading cap has been replaced.

DESCRIPTION OF PREFERRED EMBODIMENTS

Figure 1:
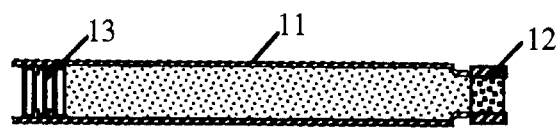
FIG. 1 is a diagrammatic axial section of piston-activated fluid-filled cartridge with a leading penetrable cap.

FIG. 1 shows a piston-activated fluid-filled cartridge 11 with a leading penetrable cap 12 and a trailing piston 13.

Figure 2:
FIG. 2 is a diagrammatic axial section of piston-activated fluid-filled cartridge with an attached leading hollow-bore steel needle.

FIG. 2 shows a piston-activated fluid-filled cartridge 11 with an attached leading hollow-bore steel needle 21 covered by a fitting rigid puncture-resistant cone 22, a bore filled with fluid 23, and a piston 13 with a trailing threaded projection 24.

Figure 3:
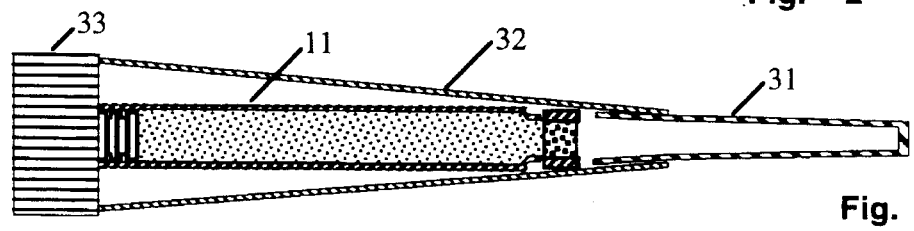
FIG. 3 is diagrammatic axial section of piston-activated fluid-filled cartridge dispensed in a three part sterile and shielding container.

FIG. 3, shows a piston-activated fluid-filled cartridge 11 dispensed in a three part sterile and shielding container comprising a leading rigid puncture-resistant hollow cone 31, a middle semi-rigid puncture-resistant hollow cone 32 and a trailing removable cap 33.

Figure 4:
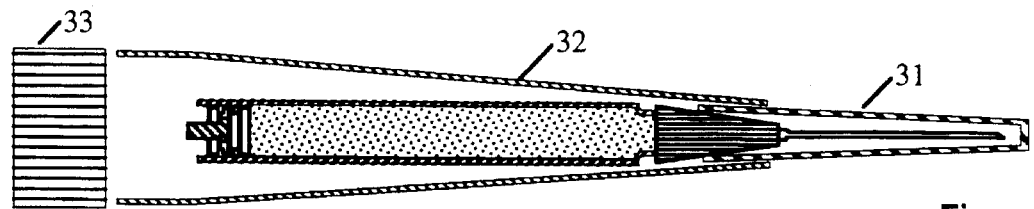
FIG. 4 shows a trailing removable cap taken off the shielding system.

FIG. 4 shows said trailing removable cap 33 taken off.

Figure 5:
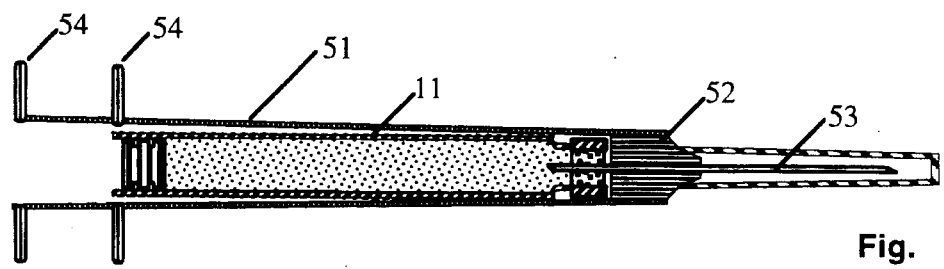
FIG. 5 shows piston-activated fluid-filled cartridge inserted into a hollow cylindroid having paired external circular flanges on the trailing end.

FIG. 5 shows a piston-activated fluid-filled cartridge 11 inserted into a hollow cylindroid 51 with a leading end 52 containing an attached double-ended needle 53, and a trailing end with paired external circular flanges 54 spaced a finger's breadth apart.

Figure 6:
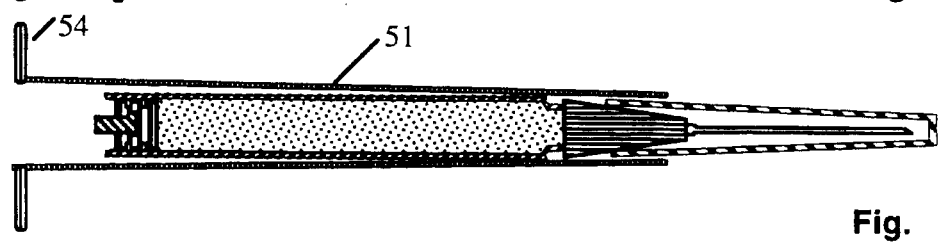
FIG. 6 shows a hollow cylindroid containing a cartridge with an attached needle, as shown in FIG. 4, and having a single external circular trailing flange.

FIG. 6 shows a hollow cylindroid 51 containing a cartridge with an attached needle, as shown in FIG. 4, and having a single external circular trailing flange 54.

Figure 7:
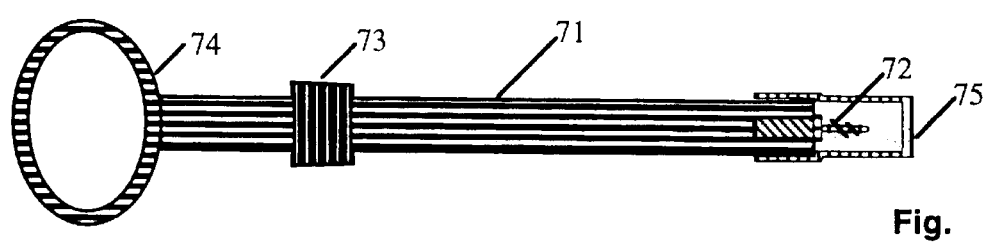
FIG. 7 shows a reusable plunger with a leading corkscrew, a sliding sleeve, a trailing thumb-ring, and a cap covering the corkscrew.

FIG. 7 shows a reusable plunger 71 with a leading corkscrew 72, a sliding sleeve 73, a trailing thumb-ring 74, and a cap 75 covering said corkscrew.

FIG. 8 shows said plunger 71 inserted into said hollow cylindroid 51 and reversibly attached to said piston 23 in said cartridge 11 by means of said corkscrew; while said sliding sleeve 73 stabilizes said plunger in the trailing bore of said hollow cylindroid 51.

FIG. 9 shows said fluid depleted cartridge 91 inside said hollow cylindroid 51, after said hollow cylindroid 51 is inserted into the remains 31,32 of said three-part shielding system. A single trailing thumb-piece 92, instead of a trailing thumb ring is shown on the reusable plunger 71.

FIG. 10 shows a safely shielded disposable combination of the spent cartridge, leading hollow-bore steel needle, hollow cylindroid and shielding system, after projecting threads 24 on the trailing end of the cartridge piston 23 have been unscrewed from a mating receptacle in the leading end of the separate reusable plunger, as shown at 111 in FIG. 11. FIG. 11 shows said separate reusable plunger 71 after the leading cap 75 has been replaced to cover a leading threaded receptacle 111 suitable for mating with a threaded trailing projection on a piston, a corkscrew, a harpoon or other means of reversible attachment between said piston 13,23 and reusable plunger 71.

In operation, the user a. removes said trailing cap from said shielding system, b. uses said leading rigid hollow puncture-resistant cone as a ramrod to eject said sterile piston-activated cylindric fluid-filled cartridge from said semi-rigid puncture-resistant cone, c. inserts said piston-activated cylindric fluid-filled cartridge into said trailing bore of said hollow cylindroid, d. uses said removable cap on said leading end of said separate reusable plunger to advance said piston-activated cylindric fluid-filled cartridge into said leading bore of said hollow cylindroid, e. removes said removable cap to proceed with said reversible attachment of said leading end of said separate reusable plunger to said trailing end of said piston in said piston-activated cylindric fluid-filled cartridge, f. slides said sliding sleeve on said separate reusable plunger forward until said sleeve becomes wedged into said trailing bore of said hollow cylindroid, g. uses said assembly to aspirate tissue fluid from a patient or to inject cartridge-contained fluid into a patient via said leading hollow-bore steel needle, h. after said leading hollow-bore steel needle is withdrawn from said patient, he/she uses one hand to insert said assembly, leading end first, into said trailing end of said semi-rigid puncture-resistant cone until the leading end of said assembly becomes wedged into the leading bore of said semi-rigid puncture-resistant cone, i. leaves said assembly lightly wedged into said semi-rigid puncture-resistant cone between uses on the same patient, or uses both hands in opposing directions to tightly wedge said assembly into said semi-rigid puncture-resistant cone, j. when an injection or series of injections is completed in the same patient and said assembly is tightly wedged into said semi-rigid puncture-resistant cone, he/she reverses procedures d-e-f to separate said separate reusable plunger from said hollow cylindroid containing what remains within or attached to said piston-activated fluid-filled cartridge, k. he/she then disposes of said hollow cylindroid and remaining contents into an appropriately placed sharps container; and retains said separate reusable plunger for reuse after proper cleansing of component parts.

Figure 12:
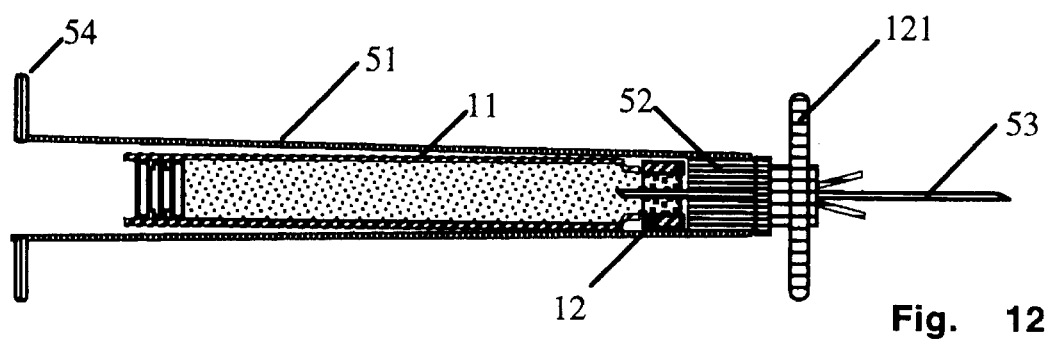
FIGS. 12–13 show a second preferred embodiment having a self-sheathing needle.
Figure 13:
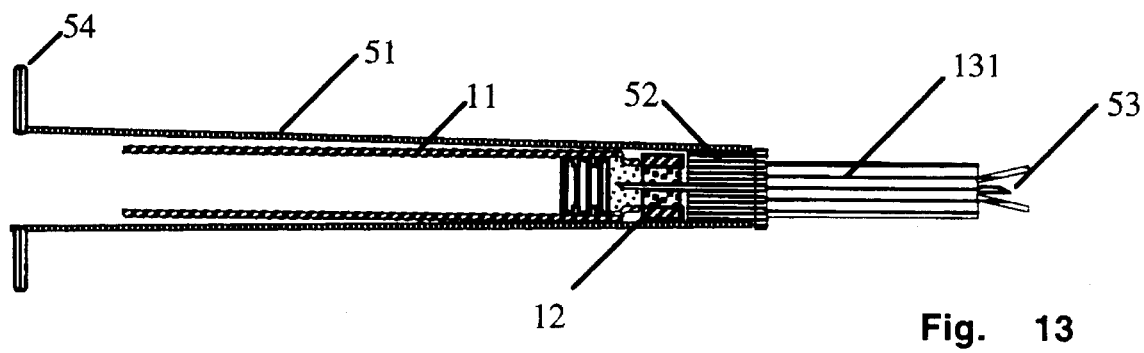

A second preferred embodiment is shown in FIG. 12–13 wherein the leading end of the hollow cylindroid 51 is closed by the hub 52 of an automatically retracting needle sheath 121,131. As shown in FIG. 12, when the needle 53 is pushed through the skin, the leading end of the sheath 121 retracts to expose the needle. As shown in FIG. 13, when the needle is withdrawn, the sheath 131 extends and locks to protect the tip of the needle 53. Usage is similar to that described in the first preferred embodiment, except:

a. The cartridge 11 is not supplied inside a three part shielding system, but should be supplied inside a sterile tamper-proof container which keeps its leading penetrable cap 12 sterile.

b. After the fluid contents of the cartridge 11 are spent and the plunger (not shown) is detached, all that remains, as shown in FIG. 13, should be disposed into a sharps container.

Although this hollow cylindroid designed for safely injecting the contents of an inserted fluid-filled cartridge has been described partly in terms of specific embodiments and auxiliary parts, such embodiments are exemplary only; and not intended to be limiting. It will be appreciated by those skilled in the art that wide variations in details can be made without departing from the spirit of the invention.

I claim:

1. A safe disposable cartridge injection assembly, useful for aspirating tissue fluid from a patient and injection of sterile fluid medication into a patient, said assembly comprising:

a) a hollow needle with a sharp leading end and a needle hub;

b) a cylindric piston-activated medicinal cartridge with a leading end and a trailing end, said leading end connecting to said needle hub and said trailing end containing a piston;

c) a reusable plunger with a leading end reversibly attachable to the piston;

d) a conical holder having an apex, a body portion and a frustum wherein:

i. said apex holds said hollow needle by means of said needle hub;

ii. said body portion holds said cylindric piston-activated medicinal cartridge, after insertion, in a conical space with an axial length longer than the length of said cylindric piston-activated medicinal cartridge, an apical bore smaller in diameter than the external diameter of said cylindric piston-activated medicinal cartridge and a frustal bore larger in diameter than the external diameter of said insertable cylindric piston-activated medicinal cartridge, such that complete insertion of said cylindric piston-activated medicinal cartridge in an apical direction into said body portion of said conical holder wedge impacts said cylindric piston-activated medicinal cartridge in a position suitable for drainage by said hollow needle;

iii. said frustum holds said reusable plunger by means of a reversible connection with a sleeve which slides over the plunger body;

iv. said body portion has external flanges near said frustum for finger placement; and e) an external shielding means which assures injection sterility and prevents injury from said hollow needle before and after use of said safe disposable cartridge injection assembly for injecting a sterile fluid into a patient.

2. The sate disposable cartridge injection assembly, as in claim 1, wherein said reusable plunger further comprises:

a. a leading means for reversible attachment to said piston within said cylindric piston-activated medicinal cartridge;

b. a leading removable cylindric cap having an external diameter at least equal to said external diameter of said cylindric piston-activated medicinal cartridge and smaller than the internal diameter of said frustum in said conical cartridge holder, an internal diameter substantially equal to the external diameter of said plunger body, and a length greater than that of said leading means for reversible attachment to said piston in said cylindric piston-activated medicinal cartridge, said removable cylindric cap being useful for enforcing said wedge impaction of said cylindric piston-activated medicinal cartridge into said body portion of said conical holder after insertion in said apical direction;

c. said plunger body having an external diameter smaller than the internal diameter of said cylindric piston-activated medicinal cartridge and a length greater than said axial length of said cylindric piston-activated medicinal cartridge;

d. said sleeve which slides over said plunger body, said sleeve having an externally conical configuration for establishing said reversible connection into said frustum of said conical holder; and e. a trailing thumb-piece on said plunger body.

3. The safe disposable cartridge injection assembly, as in claim 1, wherein said external shielding means further comprises:

a. a hollow conical shield with a closed apex resistant to puncture by said hollow needle;

b. a hollow body part longer and wider than said cylindric piston-activated medicinal cartridge;

c. said hollow body part having an internal taper coned to wedge impact said body portion of said conical holder such the leading tip of said hollow needle will be safely enclosed when said body portion of said conical holder is inserted in an apical direction insofar as possible into said hollow conical shield; and d. a frustal portion receptive to a cap for hermetic sealing, such that said hollow conical shield, when capped, can serve first as a sterile container for said cylindric piston-activated medicinal cartridge lacking a sterile tamper-proof leading cap; second, after uncapping, as a sterile holder for the leading end of said sale disposable cartridge injection assembly before or between uses on a given patient; and third as a sale container into which said body portion of said conical holder can be wedge impacted for safe disposal alter disconnection of said reusable plunger.

4. The safe disposable cartridge injection assembly, as in claim 1, wherein;

a. said apex of said conical holder comprises said needle hub having said hollow needle having a sharp trailing end which extends to puncture a penetrable diaphragm in said leading end of said cylindric piston-activated medicinal cartridge;

b. said external flanges for finger placement on said body portion of said conical holder comprises two annular flanges spaced a finger's breadth apart; and c. a trailing thumb-piece on said plunger body comprises a thumb-ring, such that said reusable plunger is operable with one hand for aspiration, as well as injection fluid.

5. The safe disposable cartridge injection assembly, as in claim 1, wherein;

a. said apex of said conical holder further comprises a hollow cone slip connecting over said needle hub when said hollow needle is permanently connected to drain said cylindric piston-activated medicinal cartridge;

b. said external flanges on said body portion of said conical holder for finger placement comprising a single annular flange with eccentric projections operable by two fingers; and c. a trailing thumb-piece on said plunger body comprises comprising a flat thumb-piece operable with two fingers for aspiration of tissue fluid and with one finger for injection of sterile medication.

6. The safe disposable cartridge injection assembly, as in claim 1, wherein said frustum of said conical holder further comprises a trailing hollow cone into which said sleeve having an external conical configuration, slides over said plunger body, slip connects and becomes impacted, such that rotation and advancement of said sleeve is precluded, while rotation and advancement of said plunger body inside said sleeve is not impaired.

7. The safe disposable cartridge injection assembly, as in claim 1, wherein said reusable plunger has a leading end reversibly attachable to said piston in said cylindric piston-activated medicinal cartridge by means of a threaded projection from an end of said piston which mates with receptive threads in the leading end of said plunger body.

8. The safe disposable cartridge injection assembly, as in claim 1, wherein said leading end of said reusable plunger is reversibly attachable to said piston in said cylindric piston-activated medicinal cartridge by means of a cork screw.

* * * * *